(12) United States Patent
Hodeau et al.

(10) Patent No.: US 8,155,267 B2
(45) Date of Patent: Apr. 10, 2012

(54) DEVICE FOR THE X-RAY ANALYSIS OF A SPECIMEN, COMPRISING AN ENERGY/ANGLE-FILTERING DIFFRACTION ANALYSER SYSTEM

(75) Inventors: Jean-Louis Hodeau, Grenoble (FR); Pierre Henri Michel Bordet, Seyssinet-Pariset (FR); Alessandra Gianoncelli, Paris (FR); Luc Ortega, Grenoble (FR); Alain Prat, Laissaud (FR); Philippe Walter, Saint Cloud (FR); Joseph Salomon, Paris (FR); Eric Dooryhe, St Egreve (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 246 days.

(21) Appl. No.: 12/593,908

(22) PCT Filed: Mar. 27, 2008

(86) PCT No.: PCT/EP2008/053618
§ 371 (c)(1),
(2), (4) Date: Sep. 29, 2009

(87) PCT Pub. No.: WO2008/125450
PCT Pub. Date: Oct. 23, 2008

(65) Prior Publication Data
US 2010/0135457 A1    Jun. 3, 2010

(30) Foreign Application Priority Data
Mar. 30, 2007 (FR) ..................... 07 54151

(51) Int. Cl.
*G01N 23/223* (2006.01)
*G01N 23/20* (2006.01)

(52) U.S. Cl. ............................ 378/44; 378/70
(58) Field of Classification Search .................. 378/44, 378/45, 46, 70, 82–85
See application file for complete search history.

(56) References Cited

U.S. PATENT DOCUMENTS

| 4,131,794 A | 12/1978 | Bruninx |
| 6,937,694 B2 * | 8/2005 | Yokoyama et al. ............. 378/78 |
| 2003/0179850 A1 * | 9/2003 | Matsubara et al. ............. 378/44 |

FOREIGN PATENT DOCUMENTS

| FR | 2 579 752 | 10/1986 |
| WO | WO 96/34274 | 10/1996 |
| WO | WO 00/19187 | 4/2000 |

* cited by examiner

*Primary Examiner* — Irakli Kiknadze
(74) *Attorney, Agent, or Firm* — Blakely, Sokoloff, Taylor & Zafman (57) ABSTRACT

A device for X-ray analysis of a sample (1), including: a generation system for the generation of an X-ray beam to irradiate an analysis zone of the sample, said analysis zone defining a analysis mean plane, and the X-ray beam being emitted along a direction of incidence; a detection system for the detection, in at least one dimension, of X-rays diffracted by the irradiated analysis zone. An analyser system located between the sample and the detection system and includes an X-ray diffracting surface forming a partial surface of revolution about an axis of revolution being contained in the analysis mean plane, with the axis of revolution being distinct from the direction of incidence and passing through the centre of the analysis zone, and with the diffracting surface being oriented so as to diffract the X-rays toward the detection system.

17 Claims, 5 Drawing Sheets

DEVICE FOR THE X-RAY ANALYSIS OF A SPECIMEN, COMPRISING AN ENERGY/ANGLE-FILTERING DIFFRACTION ANALYSER SYSTEM

This is a non-provisional application claiming the benefit of International application number PCT/EP2008/053618 filed Mar. 27, 2008.

FIELD OF THE INVENTION

This present invention concerns the field of sample analysis by the use of X-rays.

More particularly, it concerns a device for the analysis of samples by X-ray diffraction.

STATE OF THE ART

X-ray diffractometry is an analysis technique based on X-ray diffraction on the material, which is used to characterise in detail the structure of a sample. This technique is used in particular to characterise the crystallographic structure of a sample, its exact composition in terms of compounds and proportions, any transformation that it may have undergone, the microstructure and size of the crystallites and their orientations, any stress, etc.

A simple device used to perform diffraction on powders or on a polycrystalline sample is the Debye-Scherrer chamber, which is composed of a monochromatic X-ray source, a sample-holder and a film in the form of a strip that surrounds the device. The X-rays are diffracted by the sample in the direction of the film, and leave traces in the form of circles to create a diffraction diagram. This device is very simple, inexpensive, and used to easily locate the position of the peaks (radius of the circular arcs on the strip), but due to the difficulty of including ad-hoc slits or filters in it, the photographic film collects all of the signal and so also collects the signal from the surroundings of the sample, making rather inaccurate the estimate of the intensity and of the width of the diffraction peaks, and therefore the corresponding structural sample analysis.

As a consequence, it has often been proposed that the film should be replaced by a mobile assembly composed of an point detector combined with slits or a filter-analyser, with this assembly allowing the collection of more accurate information at a point, in a particular diffraction direction. In order to obtain a better signal/noise ratio and a better definition of the line shapes, a crystal analyser is often used in this type of device, placed in between the sample to be analysed and the detector, which is used to filter the rays in energy and/or to collect a greater number of X-rays diffracted by the sample in order to focus them toward the point detector. Such a device has therefore enhanced the gain either in precision or intensity. However the analysis is very lengthy, since it is necessary to conduct measurements for each of the diffraction directions. It also requires precise mechanical instrumentation, since it is necessary to move the sample and/or "detector-analyser" assembly. The analysis is rendered still more difficult when the sample to be analysed is of large size or when it cannot be moved easily.

Development of one-dimensional or two-dimensional detectors ("Image Plate" type, charge-coupled device (CCD) type, etc.) has allowed to conduct studies on diffraction, fluorescence and imaging, and improved the statistical aspects of the analyses and their ease of use compared to the use of conventional films. It also results in an enormous saving of time in relation to the use of point mobile detector. Unfortunately these one-dimensional or two-dimensional detectors have little or no filtering and/or energy resolution of the received signal, which can result in a mediocre signal/background ratio, and a resulting analysis that is still too inaccurate.

One goal of the present invention is to propose a device for the analysis of a sample by X-ray diffraction that is able to overcome at least one of the aforementioned drawbacks.

A goal of the present invention is, more particularly, to propose a device for the analysis of a sample by X-ray diffraction that allows chromatic and angular filtration of the diffracted X-rays, which is compatible with a one-dimensional or two-dimensional detection system and which allows one-dimensional or two-dimensional information to be preserved.

Another goal of the present invention is to propose a simple but effective device that is suitable for the analysis of large size samples that cannot be moved.

PRESENTATION OF THE INVENTION

To this end, a device is proposed for X-ray analysis of a sample, which includes:
  A generation means for the generation of an X-ray beam to irradiate an analysis zone of the sample, said analysis zone defining a analysis mean plane, and with the X-ray beam being emitted along a direction of incidence;
  A detection means for the detection, in at least one dimension, of X-rays diffracted by the irradiated analysis zone, characterised in that it also includes an analyser system located between the sample and the detection means and including a X-ray diffracting surface forming a partial surface of revolution about an axis of revolution being contained in the analysis mean plane, with the axis of revolution being distinct from the direction of incidence and passing through the centre of the analysis zone, and with the diffracting surface being oriented so as to diffract the X-rays toward the detection means.

The arrangement and the particular shape of the analyser system in relation to the sample zone allow collection of the diffracted X-rays in a multiplicity of diffraction directions while also improving the signal/background ratio, and therefore result in a more precise analysis of the sample zone.

Preferred but not limiting aspects of the analysis device are as follows:
  the partial surface of revolution is generated by a partial rotation of a profile defined as the section of the diffracting surface in a plane containing the axis of revolution and a diffracted beam;
  the axis of revolution is substantially to the direction of incidence;
  the partial surface of revolution is generated from the mean plane by rotation of the profile about the axis of revolution by an angle of less than 360°, preferably less than 180°, and yet more preferably between 2° and 80°;
  the device also includes a fluorescence detection means for analysis of the fluorescence radiation from the sample, with the fluorescence detection means being arranged substantially perpendicular to the mean plane;
  the profile can be straight, or curved with a concave part that is oriented toward the analysis zone of the sample;
  the profile can be a portion of a logarithmic-spiral curve, with the logarithmic-spiral curve having the centre of the analysis zone as its centre, for example;
  the device also includes associated slits at the input and output of the analyser system;

the diffracting surface includes a crystalline deposit of pyrolytic graphite;

the diffracting surface includes a multilayer deposit;

the diffracting surface includes a covering of single crystals;

the diffracting surface is designed to allow an energy analysis in reflection mode;

the detection means is one-dimensional or two-dimensional; when the detection means is two-dimensional, it can have a curved detection surface forming a partial cylindrical surface having the same axis of revolution as the diffracting surface;

the X-ray generation means, the analyser system, and the detection means are fixed in relation to each other.

The proposal also includes an optical assembly that includes a diffracting surface which is meant to reflect incident X-rays, characterised in that the diffracting surface is a partial surface of revolution generated by a partial rotation of a profile about an axis of revolution, said profile forming a portion of a logarithmic-spiral curve.

DESCRIPTION OF THE FIGURES

Other features and advantages will emerge from the description that follows, which is purely illustrative and not limiting, and which should be read with reference to the appended figures.

DETAILED DESCRIPTION OF THE INVENTION

Figure 1:
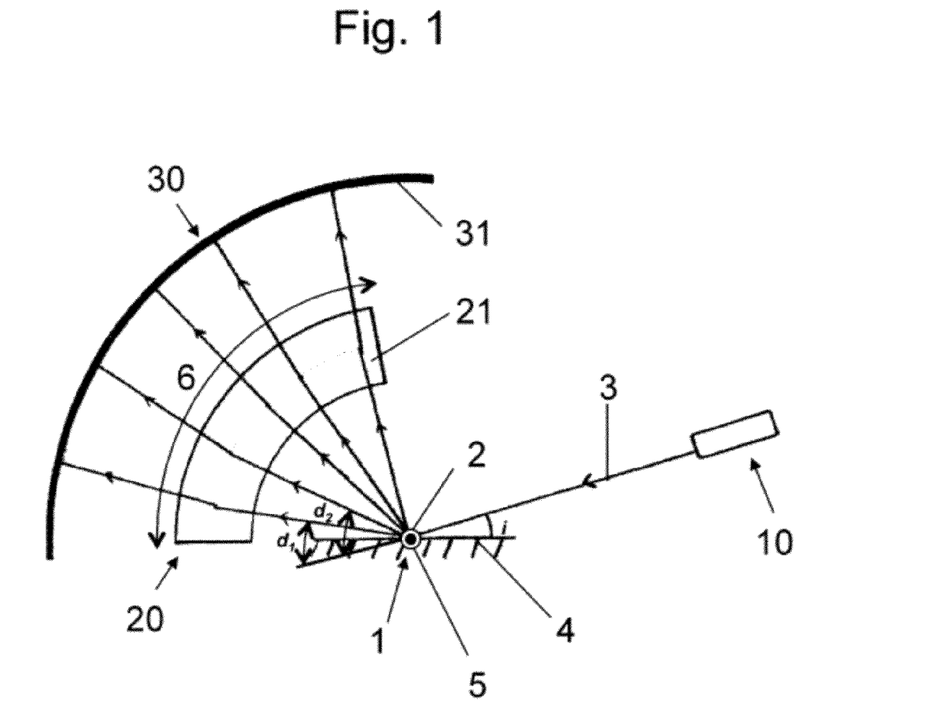
FIG. 1 is a schematic view in plane projection, parallel to the axis of revolution, of the device for the analysis of a sample by X-ray diffraction.

FIG. 1 schematically represents the analysis device of the invention, used to analyse sample 1 by X-ray diffraction.

This analysis device includes a system 10 for the generation of an X-ray beam, used to irradiate the sample 1 to be analysed. It can, for example, be used with a source of X-rays emitting monochromatic or polychromatic beams.

This source 10 shines X-rays onto sample 1 to be analysed, and more particularly onto the analysis zone 2 of sample 1 for which one is seeking to characterise the structure. Sample 1 to be analysed can be a powder, in which case the analysis zone 2 is a point one. When the analysis zone 2 is an extended surface, it forms a mean analysis plane 4. The X-ray beam is emitted along a direction of incidence 3 with an angle of incidence (i) in relation to the mean plane 4.

The X-rays diffracted by the irradiated analysis zone 2 are captured by a detection system 30, which can be one-dimensional or two-dimensional, meaning that it allows detection along at least one direction. Any type of one-dimensional or two-dimensional detector can be used, although efficient and accurate detectors of the "Image Plate" or of the Charge Coupled device (CCD) type are preferable. The detection surface 31 can also be of any shape, though a large surface is preferred once more, so as to collect a maximum of diffracted X-rays. A surface of revolution is also preferred in order to avoid a significant deformation of the diffraction diagram.

Also proposed is an analyser system 20 located between the sample 1 and the one-dimensional or two-dimensional detector 30. The primary function of this analyser system 20 is the energy filtration of the X-rays diffracted by the analysis zone 2. To this end, the analyser system has a diffracting surface 21 that is covered with a crystalline deposit whose diffracting planes perform the energy filtration. This deposit can be single-layer, like a crystalline deposit of pyrolytic graphite for example, in which case the filtering is performed by diffraction lines of the (002) type. The diffracting surface 21 can also consist of a multilayer deposit or a covering of single crystals, such as for example Si, Ge, $SiO_2$, LiF, etc., to reduce or to broaden the energy band pass. The geometry, the thickness and the nature of the surface 21 of the analyser system 20 are therefore designed to filter the beams in reflection mode. The geometry, the thickness and the nature of this diffracting surface can also be designed so as to filter the beams in transmission mode.

The analyser system 20 has further a shape and a particular arrangement that allows collection of the X-rays diffracted by the sample in a large range of diffraction directions (each of these diffraction directions j being characterised by a different diffraction angle $d_j$), then reflecting these filtered X-rays toward the detection surface 31 of the two-dimensional detector 30.

To do this, the diffracting surface 21 of the analyser system 20 is generally in the shape of a crescent with an orientation that is fixed in relation to the analysis mean plane 4.

The diffracting surface 21 is a partial surface of revolution about an axis of revolution 5, with this axis of revolution 5 passing through the centre of the analysis zone 2 with a direction that is different from the direction of incidence 3. The axis of revolution 5 is preferably distinct from the axis extending from the centre of the analysis zone 2 to the centre of the detector 30. According to a preferred mode, the axis of revolution 5 is also more or less perpendicular to the direction of incidence 3. When the analysis zone 2 is an extended surface forming an analysis mean plane 4, the axis of revolution 5 is preferably located in the analysis mean plane 4.

In addition, the diffracting surface 21 is oriented so as to reflect the X-rays toward the one-dimensional or two-dimensional detector 30, and more precisely toward the detection surface 31 of the detector 30.

The section of the diffracting surface 21 in a plane containing the axis of revolution 5 and a diffracted beam, like, for example, the analysis mean plane 4, forms a profile 23. The partial surface of revolution forming the diffracting surface 21 can also be defined as the surface generated by rotation of the profile 23 in relation to the axis of revolution 5. More preferably, the surface of revolution is partial and not total, so that the incident X-ray beam emitted by the source 10 is able to reach the sample analysis zone 2. If this surface of revolution is total, meaning that it is generated by a rotation of 360° of the profile 23 about the axis of revolution 5, then it is necessary to provide for an orifice passing through the analyser system so that the incident X-ray beam emitted by the source 10 is able to reach the sample analysis zone 2. In one particular embodiment, the surface of revolution is generated from the analysis mean plane 4 by rotation of the profile 23 in relation to the axis of revolution 5.

We will define the opening angle of the partial surface of revolution as the angle 6 corresponding to the partial rotation of the profile 23 employed to generate the diffracting surface. The larger the opening angle 6, the more the analyser system is able to capture in diffraction directions $d_j$ that are different from the X-rays diffracted by the analysis zone 2. If the opening angle is less than 180°, the device can be used to analyse the signal coming from a large size object (measurement of the nature of materials, measurement of the stresses and texture of large industrial metal parts, beams, aircraft wings, etc.). Thus, the opening angle 6 will preferably be between 0° and 180°, and according to one embodiment, more preferably between 2° and 80°. This will allow, for example, the insertion, in parallel on the same assembly, of a detection system for analysis of the fluorescence radiation emitted by the sample, with this detection system being arranged more or less perpendicular to the mean plane 4. This also allows the placement of a referencing/centring device (composed of two laser diodes for example) to allow mappings.

Figure 2:
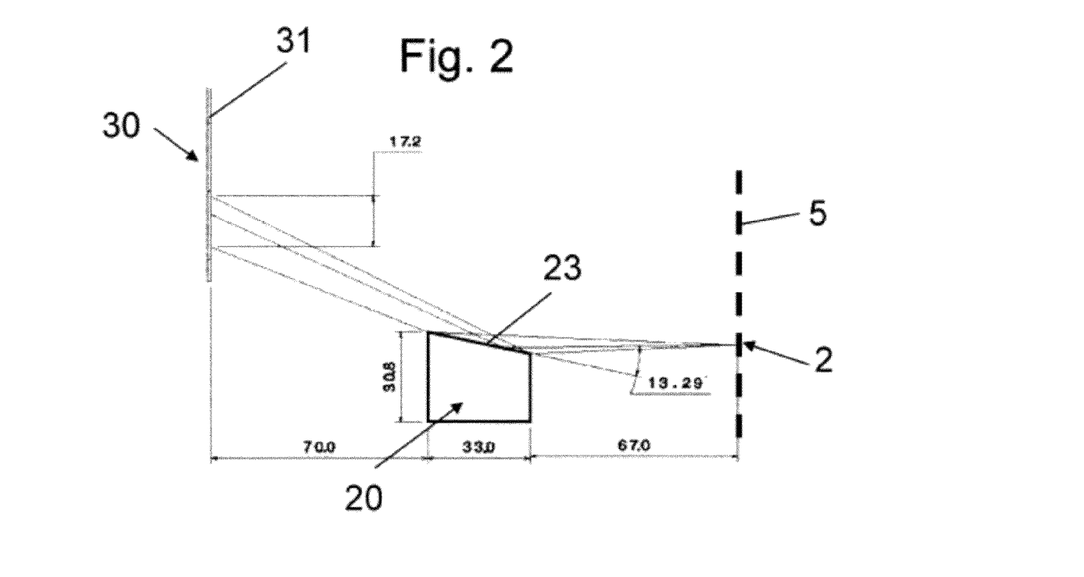
FIG. 2 is a view in section of the analyser system of an analysis device according to a first embodiment (straight diffracting section), in the analysis mean plane containing the axis of revolution.
Figure 3:
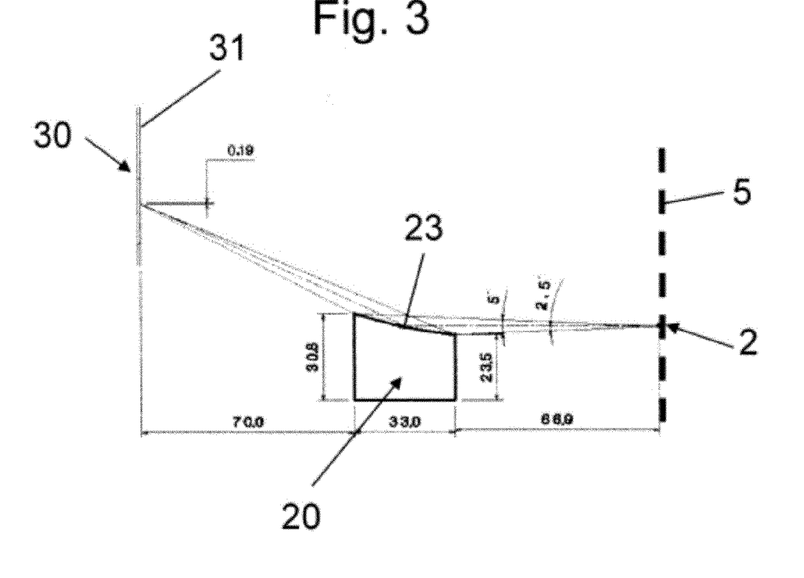
FIG. 3 is a view in section of the analyser system of an analysis device according to a second embodiment (curved diffracting section), in the analysis mean plane containing the axis of revolution.
Figure 4:
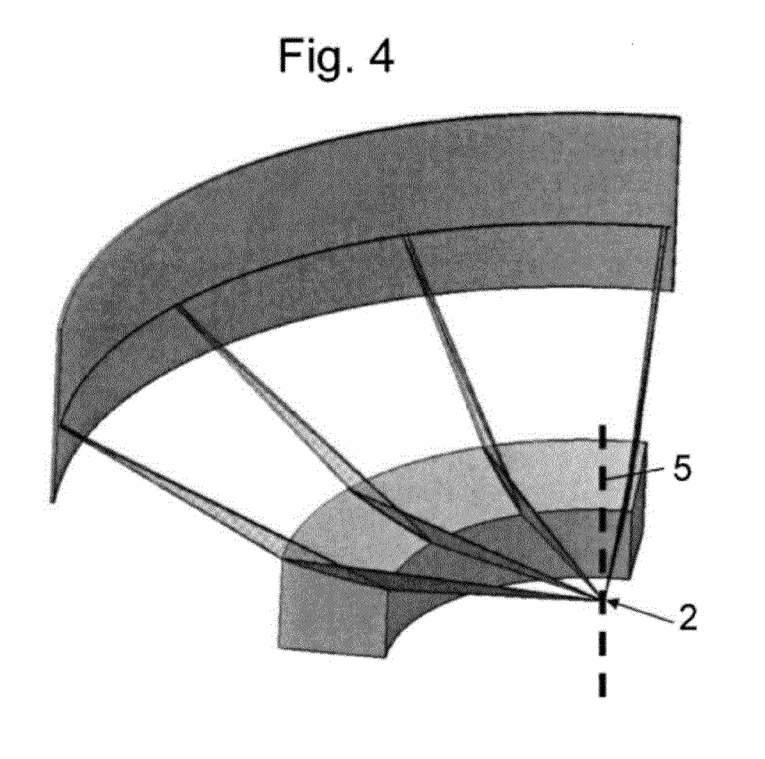
FIG. 4 is a three-dimensional representation of the analysis device of FIG. 3.

Thus, the beams coming from the sample to be analysed are diffracted by the analyser system 20 (either in reflection mode (Bragg) as in FIGS. 2, 3, and 4, or in transmission mode (Laue) with a suitable configuration/geometry) in the radial plane containing the profile 23 generating the diffracting surface 21, for all the axial directions of the beams diffracted by the sample, that is for all the diffraction directions $d_j$. It is therefore not necessary to perform rotations of the device or of the sample during the structural analysis, which greatly simplifies the adjustments and is less time consuming, while also allowing better sampling of the analysed object.

The curvature of the diffracting surface 21 also has an influence on the conditioning of the beams in the direction of the detector 30, for a given diffraction direction $d_j$.

FIG. 2 is a view in section of the analyser system of the analysis device according to a first embodiment, in a plane containing the axis of revolution and a diffracted beam, such as the analysis mean plane 4 for example. In this embodiment, the profile 23 generating the diffracting surface 21 is straight, with an inclination that allows the rays, arriving from the analysis zone 2 of the sample 1, to be reflected onto the surface of the detector 31.

An analyser system 20 with a diffracting surface 21 generated by such a straight profile allows a monochromatic analysis of the rays in all of the diffraction directions $d_j$, but for only a single angle in the perpendicular radial plane. Thus, for a given diffraction direction, the rays diffracted from the sample 1 arriving on the diffracting surface 21 with different directions of incidence are reflected only for a given energy with a direction that is also different, in accordance with the Bragg's law (see FIG. 2).

FIG. 2 represents the radial section of an analyser system 20 that has a diffracting surface 21 with a straight profile 23, for a graphite deposit and a Cu-Kalpha X radiation, with an object-detector distance of 170 mm, an analyser width of 33 mm (the analyser width corresponding to the projection of the profile 23 in the plane containing the axis of revolution and a diffracted beam, such as the analysis mean plane 4 for example) and an angular acceptance of 0.4°, which corresponds to a readout area on the detector of about 1 mm width for a given energy, the other beams corresponding to different energies. By using a wide surface on the detector, an energy band can also be analysed in order to determine, in parallel, the fluorescence and the inelastic diffusion of the sample.

According to a second embodiment, the diffracting surface 21 of the analyser system 20 is defined by a curved profile 23. One would preferably choose a profile 23 with a curvature whose concave side is oriented in the direction of the analysis zone 2 of the sample 1 (FIG. 3).

It is possible, for example, to choose a profile 23 corresponding to a portion of a logarithmic-spiral curve. More particularly, it is possible to implement a profile corresponding to a portion of a logarithmic-spiral curve having as its centre the centre of the analysis zone 2.

An analyser system 20 with a diffracting surface 21 generated from a logarithmic-spiral radial profile 23 allows not only a monochromatic analysis of the rays in all the diffraction directions $d_j$, but also a directional analysis of the source of the radial beams for each of these diffraction directions $d_j$. Thus, for a given diffraction direction $d_j$, the rays diffracted from the sample 1 arriving on the diffracting surface 21 with different directions of incidence are all reflected with the same Bragg angle and are therefore, for a suitable distance of the detector 30, semi-focused on the detection surface in a given position. In fact the orientation gradient obtained for the crystalline planes parallel to the diffracting surface of the logarithmic-spiral profile allows the fulfillment of the Bragg's law for the entire angular range of beams coming from a given quasi-point object-source (see FIG. 3). In addition to the advantages of an easier analysis associated with the partial revolution shape and the arrangement of the diffracting surface of the analyser system, this particular curvature allows an increase in the intensity of the diffracted signal, by increasing the number of rays detected, selecting a source zone to be analysed and allowing better sampling of the analysed object. It should be noted that the diffracting surface can be generated by any type of curved profile and is not limited to logarithmic-spiral profiles. In fact it is sufficient that the curved profile be suitable to focus the rays with an acceptance angle of varying width. The size of the analyser can also be designed to increase the acceptance angle of the diffracted beam, and the angular collection capacity for a given diffraction direction $d_j$ is a function of the Bragg angle of the analyser system (in the example in reflection mode presented in FIG. 3, with a graphite surface (002) and a Cu-Kalpha X radiation, the angular collection capacity can vary from 1° to about) 20°. Increasing this acceptance angle can be needed for powders with large grains, in order to improve sampling of the crystallites.

FIG. 3 represents the radial section of an analyser system 20 with a diffracting surface 21 that has a logarithmic-spiral profile 23, for a graphite deposit and a Cu-Kalpha X radiation, with a sample-detector distance of 170 mm, a width of the analyser system of 33 mm, and an angular acceptance of 5°, which corresponds to a monochromatic readout line on the detector of less than 1 mm.

FIG. 4 is a three-dimensional view schematically illustrating the detection line on the detector 30 created by the analyser system 20 in FIG. 3, having a diffracting surface 21 with logarithmic-spiral profile 23.

The two-dimensional detector 30 can be flat or curved. If its curvature is cylindrical with an axis that is collinear with the axis of revolution 5 of the diffracting surface 21, then the projection of a two-dimensional image by the curved analyser can be a strip or a line as illustrated in FIG. 4.

For experiments with diffraction on powders, tests have been performed using an analyser system, in reflection mode, with a diffracting surface formed by a straight profile (FIG. 2), and including a deposit of pyrolytic graphite on the curved surface. To filter the energies, the 002 reflection was used, with a polychromatic incident beam (copper anode tube, Cu-Kalpha line, power of 2 kW, slowing-down radiation (Bremsstrahlung) and Ni filter to eliminate the Cu-Kbeta line). For this test, the distance between the analysis zone of the sample and the analyser system was 70 mm and the analyser had a width of 30 mm. A two-dimensional detector 30 with a cylindrical detection surface was placed at a distance of 170 mm from the analysis zone of the sample, a system of slits were also used before and after the analyser system.

The angular acceptance of the analyser graphite layer is 0.4° and the width of the incident beam from the source is 0.2°. Depending on the slit, the widths of the diffraction lines are between 0.3° and 0.5°. These tests show that, in spite of the reduction in the detected signal, the use of the analyser system considerably improves the signal/background ratio.

Figure 5:
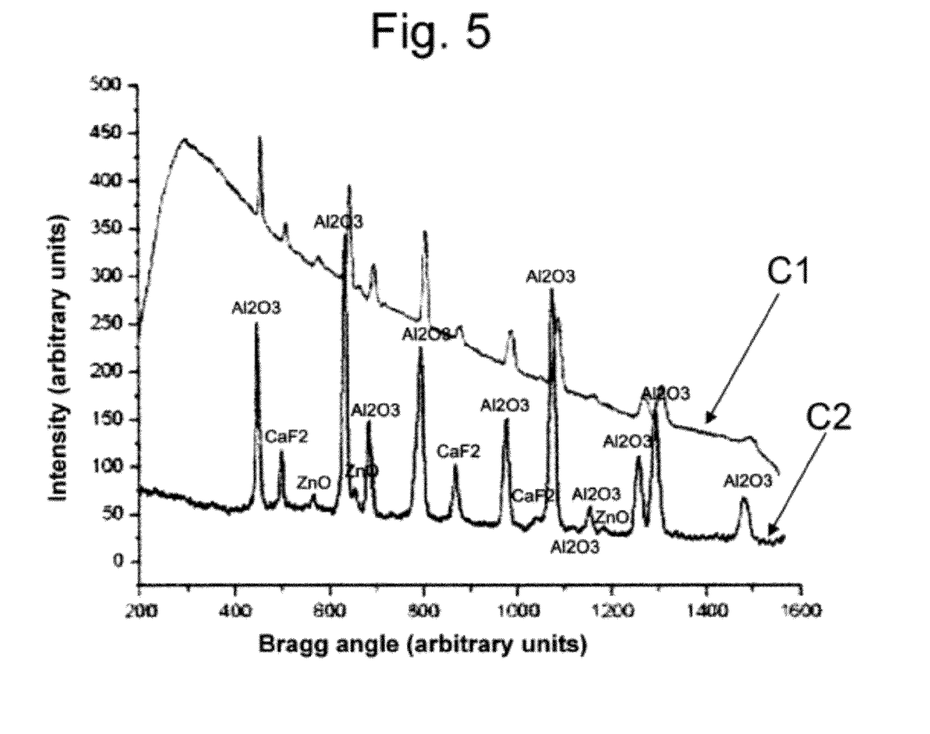
FIG. 5 places in parallel the diagrams measured with (C2) or without (C1) the analyser system, on a powder test.

FIG. 5 contains the diagrams representing the intensity measured as a function of the Bragg angle on a powder containing a test mixture (94.31% $Al_2O_3$+1.36% ZnO+4.33% $CaF_2$), with the C1 curve corresponding to the measurement performed without analyser system (intensity unit divided by 20) and the C2 curve corresponding to the measurement performed with the analyser system. In relation to the measurements without an analyser, the loss of signal on the diffracted peak is close to a factor of 8, while the background reduces by a factor of between 120 and 60, and the signal/background ratio improves by an order of magnitude. With the analyser system, the noise is almost constant as a function of the diffraction angle, as can be seen in FIG. 5. With an acquisition time of only 90 minutes, it is possible, with the analyser system, to detect the lines of all the minor phases (less than 1% weight).

Figure 6:
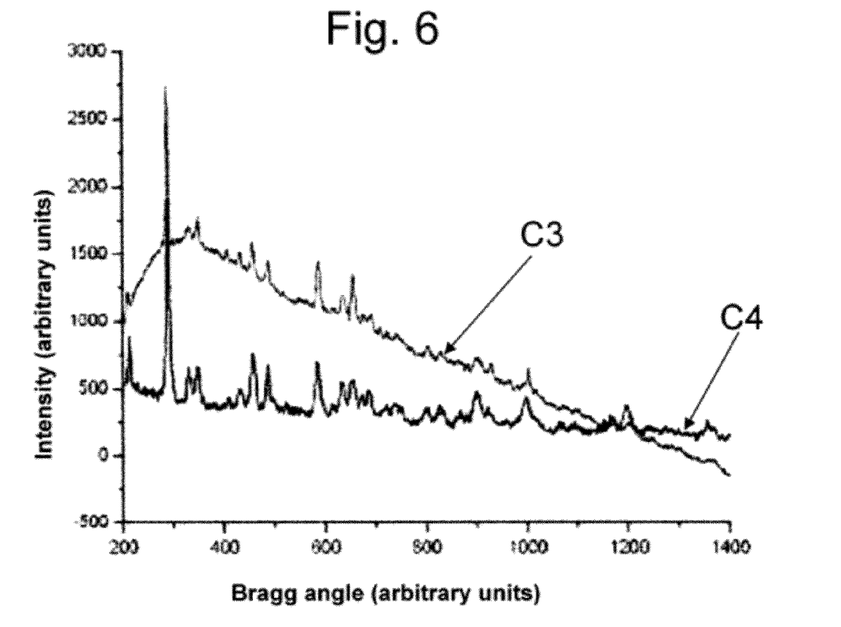
FIG. 6 places in parallel the diagrams measured with (C4) or without (C3) the analyser system, on a complex test sample.

The diagrams in FIG. 6 correspond to a measurement of 60 minutes on a complex sample of synthetic bauxite that contains 7 phases (54.90% Gibbsite+14.93% Boehmite+10.00% Haematite+9.98% Goethite+5.16% Quartz+3.02% Kaolinite+2.00% Anatase) and that generates a strong fluorescence of the iron. The C3 curve corresponds to a measurement performed without the analyser system (1500 is subtracted out from the intensity) and curve C4 corresponds to a measurement performed with the analyser system (intensity multiplied by a factor of 10). With the analysis device including the analyser system, the intensity of the lines reduced by a factor close to 8, and the noise by a factor close to 80, giving a gain in the signal/noise ratio of 10.

Figure 7:
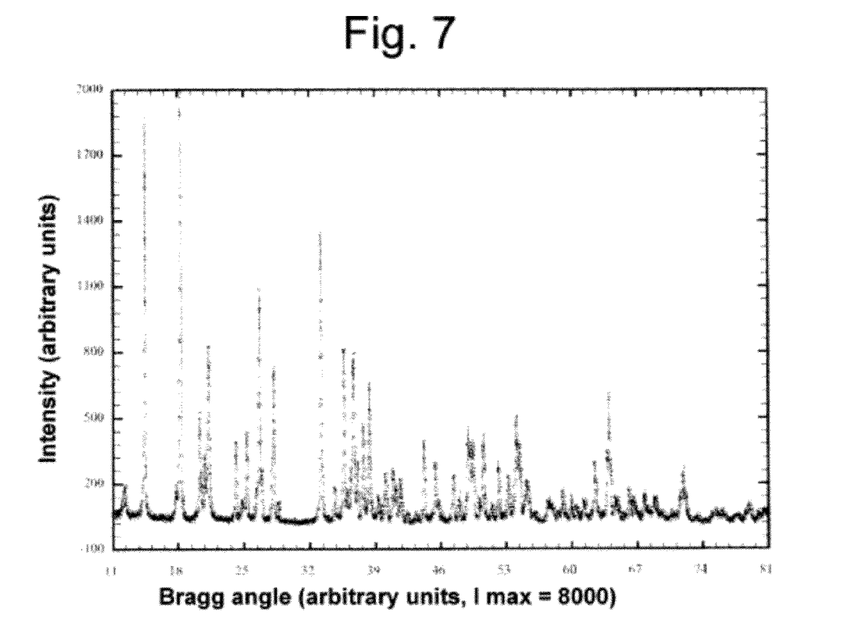
FIG. 7 is a diagram of the sample test of the diagrams in FIG. 6, measured with a high-resolution diffractometer, and a scanning "point detector-analyser" assembly.

The diagram with analyser system on this analysis device, without movement, is close to that obtained in 3 hours on a high-resolution laboratory diffractometer, by scanning the diffraction angle with a point-detector-analyser assembly. FIG. 7 illustrates the diagram obtained from a measurement performed with such a scanning device (of the Philips X'pert type) with the source being a 40 kV 40 mA tube, using the scanning of a simple analyser combined with a point-detector with a time of 3 seconds per point and an angular pitch of 0.02°.

Figure 8:
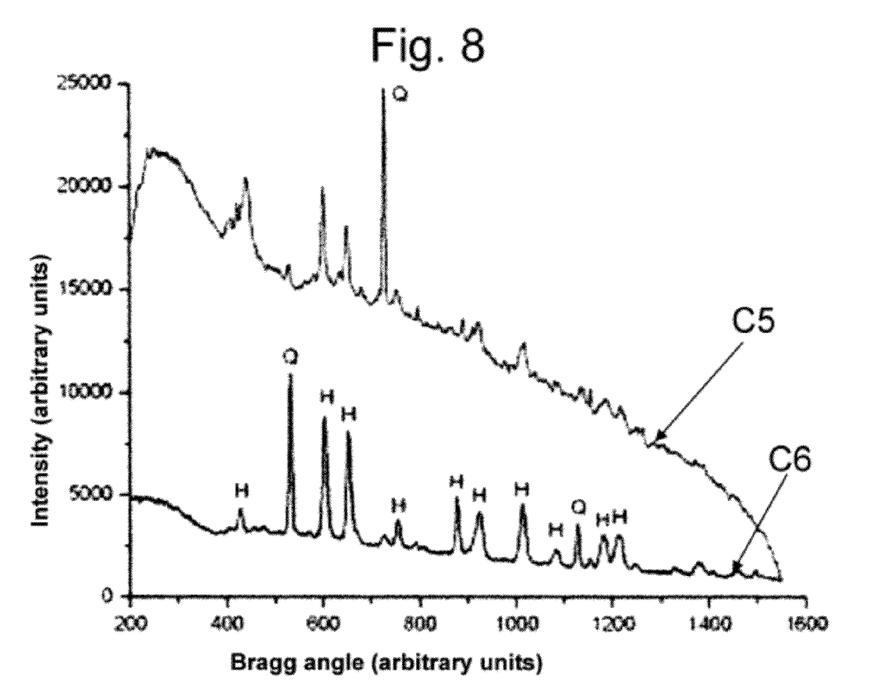
FIG. 8 places in parallel the diagrams measured with (C6) or without (C5) the analyser system, on a sample composed of large grains.

For diffraction on powders, with a fixed sample, if the grains to be analysed are large compared to the volume of the analysis zone, then sampling is very poor. The diagrams in FIG. 8 are obtained with and without the analyser system, with a straight profile, during the measurement of a mixture of haematite and large grains of quartz (0.1-0.2 mm). The C5 curve represents the measurement without analyser (intensity reduced by 10000) and curve C6 is the measurement with analyser and straight profile (intensity multiplied by a factor of 10). In fact it can be seen in this figure that the intensities of the quartz lines are not reproducible. However this drawback, which is intrinsic to diffraction, can be minimised by increasing the acceptance angle of the analyser system by replacing the straight radial profile forming the diffracting surface with a curved profile allowing focusing of the radial rays at a given point, such as a logarithmic-spiral radial profile for example, having as its focal centre the position of the object to be analysed. In this case, in reflection mode, the acceptance angle of the graphite deposit will vary between 0.4° and 5-20°, which is the equivalent of an ad-hoc rotation of the sample. Moreover, this logarithmic-spiral profile shape results in a potential intensity gain of 12-50.

Figure 9:
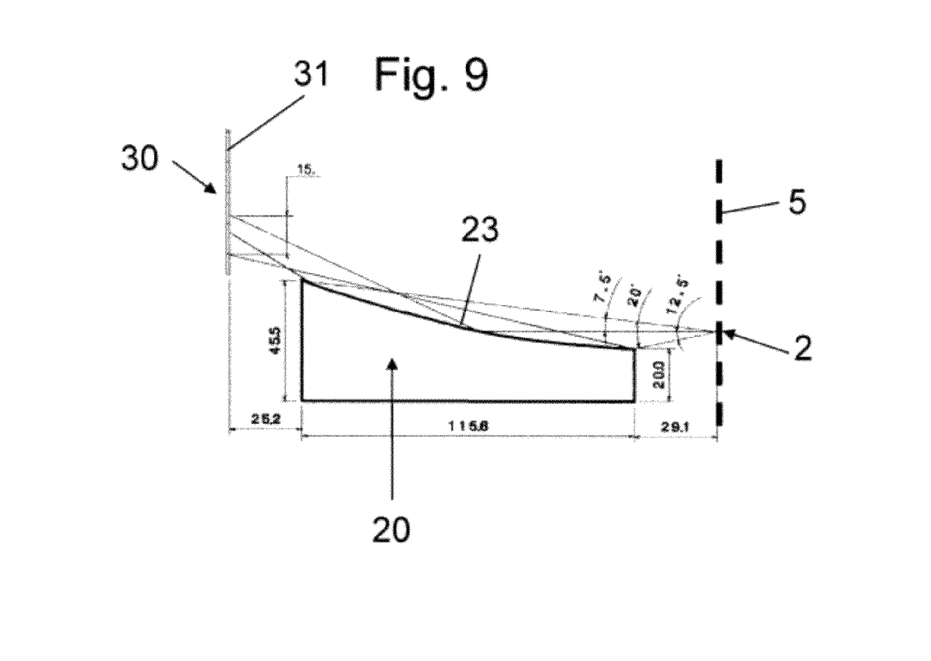
FIG. 9 is a view in section of the analyser system of an analysis device according to a third embodiment (curved diffracting section of large dimension), in the analysis mean plane containing the axis of revolution.

By using a logarithmic-spiral profile, and increasing the width of the analyser system, it is possible to create an assembly with a wider acceptance angle (with the graphite and the Cu-Kalpha radiation in reflection mode of the order of) 20°. FIG. 9 is a view in section of such a device, in which the distance between the analysed zone of the sample and the analyser system is 29.1 mm, with the analyser having a width of 115.6 mm and the two-dimensional detector being placed at a distance of 170 mm from the analysis zone of the sample. The modelling performed from such an analysis device, in relation to the measurements without analyser, shows a potential gain in the intensity of the lines (50/8) that is close to 6, and a reduction in the noise (50/80) that is close to ½. In this configuration, the image on the film is a band with a width of about 15 mm. By a displacement of the cylindrical detector of the object, it is possible to broaden the detection area, and to preserve a deformed data of the diffraction image. The proposed device therefore allows energy filtering, while also preserving (with a deformation) two-dimensional data that can be used for characterisation of the sample, this configuration can be used in particular to filter 2D diffraction diagrams of single crystals.

If it is desired to transform that two-dimensional image of the object into a line on the detector, it is possible to use a device with a logarithmic-spiral profile analyser system of shorter length, and therefore of smaller acceptance angle of 5° or even 10°. Regarding the measurements without analyser, such a device would potentially give a gain of intensity of the lines (12/8-25/8) close to 1.5-3 and a reduction in the background (12/80-25/80) close to ⅛-¼. In this configuration, the image on the film is a line with a width less than 1 mm (FIG. 3). This type of configuration allows diffraction analyses of powders in series only by a linear movement of the cylindrical detector parallel to its axis.

The use of such a chromatic and angular filtration system with a straight profile or a logarithmic-spiral profile diffracting surface therefore significantly improves the signal/background noise. With a curved profile, and more particularly a logarithmic-spiral profile, it is possible to gain in intensity while also improving the sampling of the object to be analysed. Note that this device can operate either in reflection mode (Bragg) as in FIGS. 2, 3, and 4, or in transmission mode (Laue), with a suitable configuration/geometry, taking account in particular of the axis of revolution and/or of the logarithmic-spiral curvature or any other configuration. Also, according to the shape and the particular arrangement of the analyser system, a diffractometer/fluorescence-meter can be designed without any moving parts, that also allows a parallel measurement of fluorescence and the use of a centring device for the analysed point of the object surface.

The proposed analyser system has a very wide range of applications, since it can be combined with multiple diffraction set-ups using a two-dimensional detector. This includes:

- diffraction of powders (analysis of phases, Rietveld and Pair Distribution Function (PDF) analyses, which are important not only in many laboratories and industries in the fields of chemistry and materials science, but also for studies on large instruments (synchrotrons, neutrons, etc.), in particular in order to reduce the background associated with fluorescence, inelastic diffusion and the environments of the sample,
- biocrystallography and single crystal analyses (by energy filtering the diffraction images with a deformation of the latter), in order to reduce the background noise, for solving structures and, for example, for collecting Multi-wavelength Anomalous Diffraction data (MAD) with synchrotron radiation,
- single crystal diffraction, for surfaces or in-situ experiments, to reduce the background noise coming from sample enclosures, the environment or fluorescence.

With the curvatures and arrangements of the two-dimensional analysers/detectors that are used for optical conversion of a "2D image" into a "1D line", and the associated slits, the applications include:

- kinetic studies or serial studies on powders, in which a sector (5° to 10°) of each Debye ring is focused on a point, with the full powder diagram being projected onto a line, this concerns applications in the chemistry of solids, in pharmacology, and in microstructures mappings;
- the creation of portable diffractometer/fluorescence-meters with the advantage of good signal/background noise ratios of the analyser system combined with a gain of flux and better sampling associated with the logarithmic-spiral curvature of the diffracting surface profile; as illustrated by the tests, such a diffractometer/fluorescence-meter with no moving parts and that is portable can be used for the analysis of multi-phase materials, and can therefore be applied to mobile studies on archaeological sites (wall analysis), industrial worksites (checking and monitoring of production equipment) and also directly on very large industrial objects (texture, stresses in rails, wing behaviour, etc.).
- the measurement of X-ray fluorescence, if the source is close to a point one, and with the inclusion of slots, in order to be able to select an energy (logarithmic-spiral profile diffracting surface) or an energy range (diffracting surface with straight profile or curved profile with angle gradient), the latter profile is able to provide a new X-ray spectroscopy wavelength dispersion device.
- imaging measurements, if the source is close to a point one and if the detector 30 is outside the quasi-focussing distance of the analyser, in order to be able to remove the inelastic diffusion and the fluorescence (logarithmic-spiral profile diffracting surface); when the source is at infinity, a plane analyser suffices.

Note that the device presented with analyser system could also be suitable to be used for sample analysis by neutron beams.

The reader will understand that a large number of modifications can be made to the invention without materially moving outside of the new information and advantages described here. As a consequence, any modification of this type are intended to be incorporated within the scope of the analysis device and of the analyser system described.

The invention claimed is:

1. A device for X-ray analysis of a sample, including: A generation system for the generation of an X-ray beam to irradiate an analysis zone of the sample, said analysis zone defining a analysis mean plane, and the X-ray beam being emitted along a direction of incidence; A detection system for the detection, in at least one dimension, of X-rays diffracted by the irradiated analysis zone, wherein the device further includes an analyser system located between the sample and the detection system and including a X-ray diffracting surface forming a partial surface of revolution about an axis of revolution being contained in the analysis mean plane, with the axis of revolution being distinct from the direction of incidence and passing through the centre of the analysis zone, and with the diffracting surface being oriented so as to diffract the X-rays toward the detection system.

2. The device of claim 1, wherein the partial surface of revolution is generated by a partial rotation of a profile defined as the section of the diffracting surface in a plane containing the axis of revolution and a diffracted beam.

3. The device of claim 2, wherein the profile is straight.

4. The device of claim 2, wherein the profile is curved with a concavity oriented toward the analysis zone of the sample.

5. The device of claim 2, wherein the profile is a portion of a logarithmic-spiral curve.

6. The device of claim 5, wherein the logarithmic-spiral curve has a centre corresponding to the centre of the analysis zone.

7. The device of claim 1 wherein the axis of revolution is substantially perpendicular to the direction of incidence.

8. The device of claim 1, wherein the partial surface of revolution is generated from the mean plane by rotation of the profile about the axis of revolution, by an angle less than 360°, preferably less than 180°, and yet more preferably between 2° and 80°.

9. The device of claim 8, further including a fluorescence detection system for analysis of the fluorescence radiation emitted by the sample, with the fluorescence detection system being arranged substantially perpendicular to the mean plane.

10. The device of claim 1, further including associated slits at the input and output of the analyser system.

11. The device of claim 1, wherein the diffracting surface includes a crystalline deposit of pyrolytic graphite.

12. The device of claim 1, wherein the diffracting surface includes a multilayer deposit.

13. The device of claim 1, wherein the diffracting surface includes a covering of single crystals.

14. The device of claim 1, wherein the diffracting surface is designed to allow energy analysis in reflection mode.

15. The device of claim 1, wherein the detection system is one-dimensional or two-dimensional.

16. The device of claim 1, wherein the detection system is two-dimensional and has a curved detection surface forming a partial cylindrical surface with the same axis of revolution as the diffracting surface.

17. The device of claim 1, wherein the generation system, the analyser system, and the detection system are fixed with respect to each other.

* * * * *